US00PP30776P2

(12) United States Plant Patent
Stemkens

(10) Patent No.: US PP30,776 P2
(45) Date of Patent: Aug. 6, 2019

(54) ***LEUCANTHEMUM* PLANT NAMED 'LEUZ0005'**

(50) Latin Name: *Leucanthemum maximum*
Varietal Denomination: LEUZ0005

(71) Applicant: SYNGENTA PARTICIPATIONS AG, Basel (CH)

(72) Inventor: Henricus Godefridus Wilhelmus Stemkens, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/999,986

(22) Filed: Sep. 6, 2018

(51) Int. Cl.
*A01H 5/02* (2018.01)
*A01H 6/14* (2018.01)

(52) U.S. Cl.
USPC ..... Plt./285

(58) Field of Classification Search
USPC ..... Plt./285
See application file for complete search history.

*Primary Examiner* — Annette H Para
(74) *Attorney, Agent, or Firm* — Dale Skalla

(57) ABSTRACT

A new *Leucanthemum* plant named 'LEUZ0005' characterised particularly as to novelty by the fact that it does not need cold to flower, has abundant flowers on a large plant and has very big flowers from which the petals have an upward direction.

1 Drawing Sheet

Varietal denomination: 'LEUZ0005'.

BACKGROUND OF THE NEW PLANT

The present invention comprises a new distinct cultivar of *Leucanthemum*, botanically known as *Leucanthemum maximum*.

The new *Leucanthemum* is a product of a planned breeding program conducted in Enkhuizen, The Netherlands. The objective of the breeding program was to develop a new *Leucanthemum* cultivar that is floriferous, single-flowering, good flower quality and a good vigor that does not require cold to flower.

The present cultivar originated from an open pollinated cross made in 2011 of a *Leucanthemum* genetic pool selection identified as 'N5012-1', not patented, as the female , or seed parent, with a *Leucanthemum* genetic pool selection identified as 'M5996-5', not patented, as the male, or pollen parent.

The present cultivar has been repeatedly asexually reproduced by cuttings in in Enkhuizen, The Netherlands.

The distinctive characters of this new *Leucanthemum* are stable and reproduced true to type in successive generations of asexual reproduction. It takes 10 to 14 weeks to produce a finished plant, depending on the temperature and day length.

This new *Leucanthemum* plant is a perennial in all climatical zones in the US.

BRIEF DESCRIPTION OF THE PHOTOGRAPHS

Figure 1:
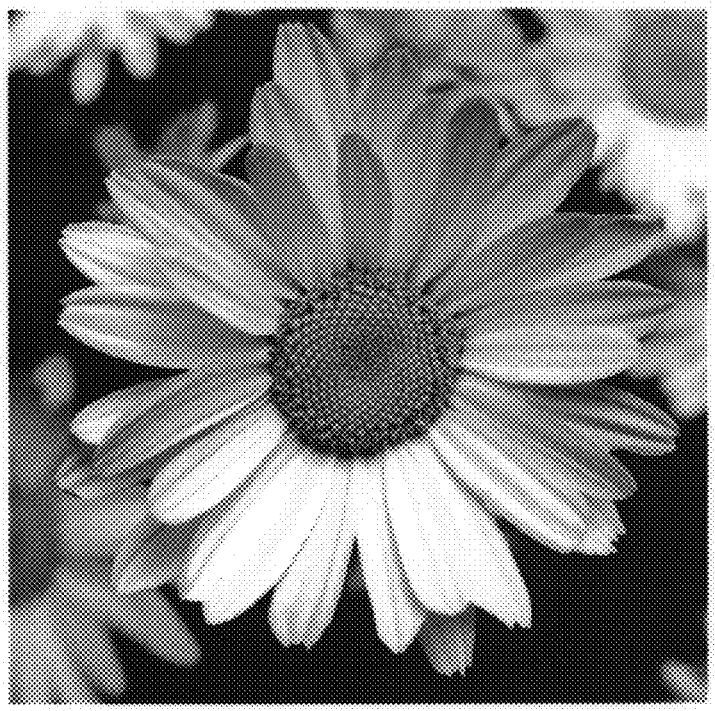
Figure 2:
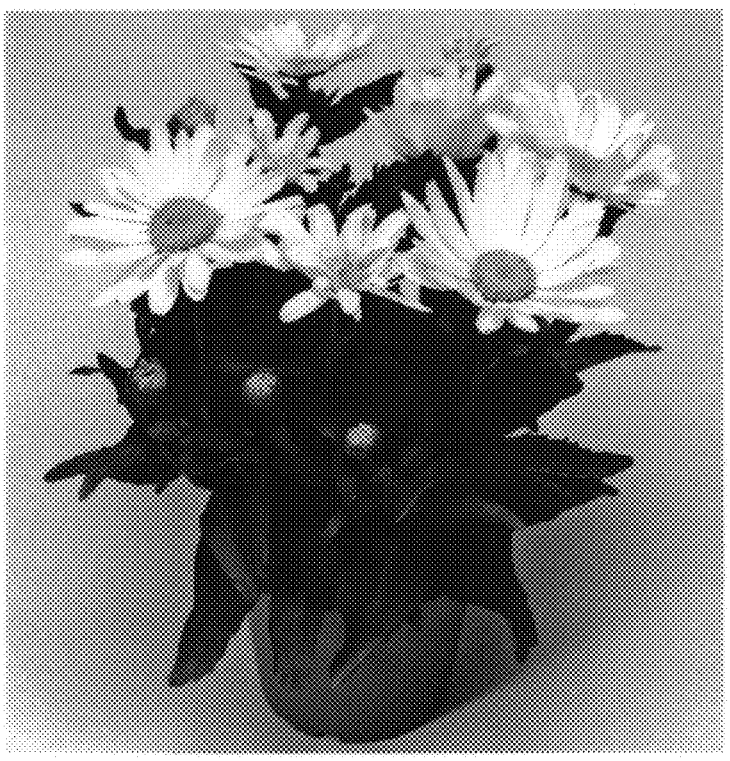

This new *Leucanthemum* plant is illustrated by the accompanying photographic drawings of which one shows blooms, buds and foliage of the plant in full color, the color showing being as true as can be reasonably obtained by conventional photographic procedures. The photographic drawings show in FIG. 1 a close-up of the flower and in FIG. 2 a whole flowering plant.

DETAILED DESCRIPTION

The following detailed descriptions set forth the distinctive characteristics of this new *Leucanthemum*. The data which defines these characteristics were collected from asexual reproductions carried out in Enkhuizen, The Netherlands. The plant description was taken on 14 weeks old plants, blossomed under natural light on the container field.

A Plant Breeder's Right for this cultivar has not yet been applied for. 'LEUZ0005' has not been made publicly available prior to the effective filing date of this application, notwithstanding any disclosure that may have been made less than one year prior to the effective filing date of this application by the inventor or another who obtained 'LEUZ0005' directly from the inventor.

Plants of the new *Leucanthemum* and the female parent differ in:

- Flower size is bigger than the female parent.
- Plant height is taller than the female parent.
- Direction of the petals. Petals are 30 degrees upward directed while the female parent has flat petals.

Plants of the new *Leucanthemum* and the male parent differ in:

- Flower size is bigger than the male parent.
- Branching is having more branches than the male parent.
- Flower color is more white while male parent is more cream white.

Natural flowering season at specified location(s): Under Northern European conditions, 'LEUZ0005' flowers from June until the end of September The following traits distinguish 'LEUZ0005' as a new and distinct cultivar:

- The plant does not require cold to flower.
- The flowers are single.
- The flowers are abundant.
- The flowers are very big.

Color references are made to The Royal Horticultural Society Colour Chart (R.H.S.) 2001.

Plants of the new *Leucanthemum* can be compared to plants of 'LEUZ0001', U.S. Plant Pat. No. 23,426. In side-by-side comparisons conducted by the inventor in Enkhuizen, The Netherlands, the plants of the new *Leucanthemum* differed from the plants of the cultivar 'LEUZ0001' in the following characteristics:

TABLE 1

Differences between the new cultivar 'LEUZ0005' and a similar cultivar

| | 'LEUZ0005' | 'LEUZ0001' |
|---|---|---|
| Flower type: | Single flowering | Double flowering |
| Plant height: | Taller | Shorter |
| Leaf color: | Dark green | Light green |

The plant:

*Parentage.*—

*Female parent.*—'N5012-1', a genetic pool selection, not patented.

*Male parents.*—'M5996-5', a genetic pool selection, not patented.

Propagation:

*Type cutting.*—Terminal cuttings.

*Time to initiate roots.*—21 days at 20 degrees C.

*Time to produce rooted cutting.*—3.5 weeks.

*Root description.*—Fine, fibrous, and white in color.

Plant description:

*General appearance.*—Big plant with abundant flowers plant with dark leaves early to flower.

*Branching habit.*—Basal branching.

*Plant height.*—42 cm.

*Plant spread.*—20 cm.

*Lateral branch description.*—

*Length.*—

*Primary.*—28 cm.

*Secondary.*—14 cm.

*Diameter.*—

*Primary.*—0.4 cm.

*Secondary.*—0.3 cm.

*Texture.*—Smooth, glabrous.

*Internode length.*—2.5 cm.

*Color.*—RHS 137A.

Foliage description:

*Arrangement.*—Alternate.

*Length, mature leaves.*—12 cm.

*Width, mature leaves.*—3.5 cm.

*Shape.*—Lanceolate.

*Apex.*—Rounded to broadly acute.

*Base.*—Attenuate.

*Aspect.*—Arcuate.

*Margin.*—Dentate.

*Pubescence.*—

*Upper surface.*—Lightly pubescent.

*Lower surface.*—Lightly pubescent.

*Texture.*—Smooth, glabrous.

*Color young foliage, upper surface.*—RHS 137A.

*Color young foliage, lower surface.*—RHS 137B.

*Fully expanded foliage, upper surface.*—RHS 137A.

*Fully expanded foliage, lower surface.*—RHS 138A.

*Petiole.*—Absent.

*Veins, venation type.*—Pinnate.

*Veins, color upper surface.*—RHS 143A.

*Veins, color lower surface.*—RHS 143D.

Inflorescence:

*Bud (described before colour developed).*—

*Bud shape.*—Spherical.

*Bud diameter.*—1.1 cm.

*Bud length.*—0.6 cm.

*Bud color.*—RHS 137B.

*Appearance.*—

*Form.*—Actinomorphic.

*Inflorescence position.*—Terminal.

*Disc and ray floret arrangement.*—Acropetally on a capitulum.

*Number of inflorescences per plant.*—55.

*Lasting quality per flower.*—12 days.

*Fragrance.*—None.

*Size.*—

*Diameter.*—

*First flowers.*—16 cm.

*Last flowers.*—9 cm.

*Height.*—2 cm.

*Diameter of disc.*—3 cm.

Ray florets:

*Length.*—3.9 cm.

*Width.*—1.1 cm.

*Shape.*—Oblanceolate.

*Apex.*—Tridentate.

*Base.*—Cuneate.

*Margin.*—Entire.

*Texture (both upper and lower surfaces).*—Smooth, glabrous.

*Number per inflorescence.*—38.

*Color, when opening.*—Upper surface: RHS 157A. Lower surface: RHS 157B.

*Color, fully opened.*—Upper surface: RHS 157D. Lower surface: RHS 157C.

Disc florets:

*Length.*—0.9 cm.

*Width.*—0.15 cm.

*Shape.*—Elliptic.

*Number per inflorescence.*—300.

*Color.*—Immature — Apex: RHS 7B. Margin: RHS 154B.

*Mature.*—Apex: RHS 13B. Margin: RHS 7C.

Phyllaries:

*Length.*—1.1 cm.

*Width.*—0.3 cm.

*Shape.*—Elliptic.

*Apex.*—Obtuse.

*Margin.*—Entire.

*Number per inflorescence.*—44.

*Arrangement.*—Imbricate whorls.

*Texture (both upper and lower surfaces).*—Smooth and glabrous with light pubescence present.

*Color.*—Upper surface: RHS 138C. Lower surface: RHS 138B.

Peduncle:

*Length.*—7 cm.

*Diameter.*—0.4 cm.

*Aspect.*—Upright.

*Texture.*—Light pubescence present.

*Color.*—RHS 137A.

Reproductive organs:

*Androecium.*—

*Presence.*—On disc florets only.

*Number (per flower).*—1.

*Filament length.*—0.2 cm.

*Filament color*.—RHS 5B.
*Anthers*.—Shape: Oblong. Length: 0.1 cm. Color: RHS 8B.
*Pollen*.—Color: RHS 8A. Amount (generally): Moderate.
*Gynoecium*.—
*Presence*.—On disc and ray florets.
*Pistils*.—Number: 1. Length: 0.5 cm.
*Style*.—Length: 0.4 cm. Color: RHS 154C.
*Stigma*.—Shape: Bi-lobed. Color: RHS 7B.
*Seeds*.—None observed.
*Disease resistance*.—No resistance or susceptibility observed.
*Temperature tolerance*.—Cold tolerance to −20 degrees C.; Heat tolerance to 35 degrees C.
*Drought tolerance*.—Not drought tolerant.

What is claimed is:

1. A new and distinct cultivar of *Leucanthemum* plant named 'LEUZ0005', as substantially illustrated and described herein.

* * * * *